United States Patent
Mariella, Jr. et al.

(10) Patent No.: US 9,480,935 B2
(45) Date of Patent: Nov. 1, 2016

(54) SYSTEMS AND METHODS FOR SEPARATING PARTICLES AND/OR SUBSTANCES FROM A SAMPLE FLUID

(75) Inventors: Raymond P. Mariella, Jr., Danville, CA (US); George M. Dougherty, Albany, CA (US); John M. Dzenitis, Danville, CA (US); Robin R. Miles, Danville, CA (US); David S. Clague, San Luis Obispo, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 2744 days.

(21) Appl. No.: 12/024,762

(22) Filed: Feb. 1, 2008

(65) Prior Publication Data

US 2009/0194420 A1   Aug. 6, 2009

(51) Int. Cl.
  *B01D 17/06* (2006.01)
  *G01N 15/02* (2006.01)
  *G01N 1/40* (2006.01)
  *G01N 15/14* (2006.01)

(52) U.S. Cl.
  CPC ............. *B01D 17/06* (2013.01); *G01N 1/4077* (2013.01); *G01N 2001/4072* (2013.01); *G01N 2015/0288* (2013.01)

(58) Field of Classification Search
  USPC ....... 435/173.9; 204/403.01; 205/777.5, 792; 210/748.01, 748.02
  See application file for complete search history.

(56) References Cited

U.S. PATENT DOCUMENTS

| | | | |
|---|---|---|---|
| 4,877,516 A * | 10/1989 | Schram | 209/155 |
| 5,993,631 A | 11/1999 | Parton et al. | |
| 6,881,314 B1 | 4/2005 | Wang et al. | |
| 6,936,151 B1 | 8/2005 | Lock et al. | |
| 7,674,630 B2 * | 3/2010 | Siversson | 436/177 |
| 2002/0076825 A1 * | 6/2002 | Cheng et al. | 436/174 |
| 2002/0182657 A1 * | 12/2002 | Ranger | 435/7.32 |
| 2002/0198928 A1 * | 12/2002 | Bukshpan et al. | 709/200 |
| 2004/0011651 A1 * | 1/2004 | Becker et al. | 204/547 |
| 2004/0065599 A1 * | 4/2004 | Lal et al. | 209/659 |
| 2005/0106064 A1 | 5/2005 | Laurell et al. | |
| 2006/0163166 A1 * | 7/2006 | Hawkes et al. | 210/748 |

FOREIGN PATENT DOCUMENTS

WO   WO 0004978 A1 *   2/2000

OTHER PUBLICATIONS

Marina et al. "Combination Ultrasonic-Dielectrophoretic Particle Traps for Particle Trapping and Sample Purification in a Microfluidic Channel" (cont'd).
Technical Proceedings of the 2006 Nanotechnology Conference and Trade Show, Nanotech 2006 vol. 2, Boston, MA.
Hambly E, "The viriosphere, diversity, and genetic exchange within phage communities." Curr Opin Microbiol. Aug. 8, 2005. 444-450, CA.

\* cited by examiner

*Primary Examiner* — Susan D Leong
(74) *Attorney, Agent, or Firm* — Zilka-Kotab, PC

(57) ABSTRACT

Systems and methods for separating particles and/or toxins from a sample fluid. A method according to one embodiment comprises simultaneously passing a sample fluid and a buffer fluid through a chamber such that a fluidic interface is formed between the sample fluid and the buffer fluid as the fluids pass through the chamber, the sample fluid having particles of interest therein; applying a force to the fluids for urging the particles of interest to pass through the interface into the buffer fluid; and substantially separating the buffer fluid from the sample fluid.

25 Claims, 7 Drawing Sheets

Figure 1:
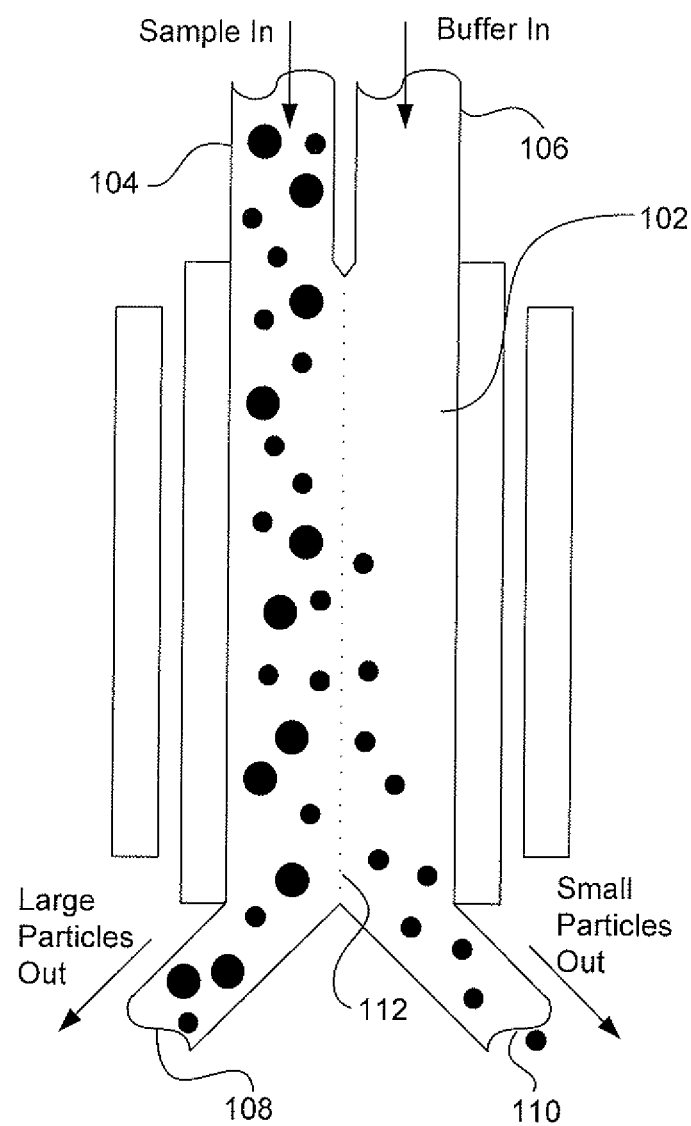

SYSTEMS AND METHODS FOR SEPARATING PARTICLES AND/OR SUBSTANCES FROM A SAMPLE FLUID

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to material separations, and more particularly, this invention relates to systems and methods for separating particles and/or substances from a sample fluid.

BACKGROUND OF THE INVENTION

Bioengineered and emerging pathogens represent a significant threat to human health. The best defense against a rapidly-expanding pandemic is to have capabilities to isolate the causative pathogen quickly from biological samples such that it can be characterized and so that tests and vaccines can be developed against it. Whether the scenario for biological analysis involves samples from the environment, food, water, agriculture, animals, or from humans, the one persistent technology gap in the process of identifying and quantifying the presence of pathogenic agents has been "the front end of assays," namely sample handling and sample preparation.

One problem encountered in sample handling is separating and concentrating small particles from complex liquid samples. This problem is of particular importance in the applications of pathogen detection and medical diagnostics, wherein separating a particle type of interest (e.g. cells, viruses, bacteria, etc.) from an obscuring background of other materials can increase the sensitivity of a diagnostic assay, and allow particles present at very low concentrations to be detected more easily. Some prior approaches have been based on passive separations relying upon differences in diffusion speeds of different particles or the ability of different particles to negotiate an array of small obstacles or openings. Simple physical filters can be included in this category.

Other approaches have used centrifugal motion to manipulate particles and drive them to separate locations, which has its advantages and disadvantages. The basic slowness and awkwardness of centrifugation is a primary problem with this sample preparation technique, but also its incompatibility with automation or high-throughput parallel processing causes this technique to suffer in the application of rapid virus and biothreat detection systems. It relies on bulky equipment and requires manual manipulation by a technician. It can also be dangerous as the high rotational speeds developed within ultracentrifuges can result in serious accidents if the equipment fails, potentially spreading aerosolized virus over a large area. Many laboratories that work with pathogenic viruses prohibit or limit the use of centrifuges for this reason.

Most standard laboratory methods for viral separation from oral-cavity samples consist of batch procedures based on centrifugation or week-long propagation of viruses. Three critical drawbacks to these techniques are: 1) clinical labs avoid ultracentrifugation of pathogenic samples due to the possibility of aerosolization of the sample (especially following potential equipment failure, as previously stated) 2) all the viruses are coalesced and further processing is required to isolate the pathogen and 3) these techniques are not amenable to quick, high-throughput processing, which may be necessary to correctly identify the pathogen in a timely fashion.

Therefore, since standard laboratory methods can not rapidly and efficiently separate or purify virus and bacteria from samples, there is an unaddressed need of national importance in rapid isolation, detection, and classification of engineered and naturally-occurring emerging bio-threats. As is true in any such biodetection process, sample preparation is a critical requirement for many biological assays and is a major bottleneck in the process of detecting and identifying biological agents. Capabilities for separation, detection, and classification of unknown species from biological samples becomes more urgent when dealing with bioengineered threats because the investigator must rapidly isolate the unknown from all the other particles in the sample to enable characterization and the development of antibody or nucleic acid-based detection assays. Viruses are an important category of pathogens because some of its members, such as influenza and smallpox, are extremely infectious and very virulent forms could result in sudden, massive pandemics. Viruses are often difficult to isolate due to their small size (typically <200 nm.), compared with the bulk of the particles in a sample.

SUMMARY OF THE INVENTION

A method for separating particles from a sample fluid according to one embodiment comprises simultaneously passing a sample fluid and a buffer fluid through a chamber such that a fluidic interface is formed between the sample fluid and the buffer fluid as the fluids pass through the chamber, the sample fluid having particles of interest therein; applying a force to the fluids for urging the particles of interest to pass through the interface into the buffer fluid; and substantially separating the buffer fluid from the sample fluid.

A method for separating a toxin from a sample fluid according to one embodiment comprises simultaneously passing a sample fluid and a buffer fluid through a chamber such that a fluidic interface is formed between the sample fluid and the buffer fluid as the fluids pass through the chamber, the sample fluid having a toxin of interest therein; applying a force to the fluids for urging the toxin of interest to pass through the interface into the buffer fluid; and substantially separating the buffer fluid from the sample fluid.

A system for separating particles from a sample fluid according to another embodiment comprises a chamber; a sample fluid inlet for introducing a sample fluid to the chamber; a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, the sample fluid having particles of interest therein; a mechanism for applying a force to the fluids for urging the particles of interest to pass through the interface into the buffer fluid; a sample fluid outlet coupled to the chamber; and a buffer fluid outlet coupled to the chamber, the buffer fluid being substantially separated from the sample fluid.

A system for separating a toxin from a sample fluid according to another embodiment includes a chamber; a sample fluid inlet for introducing a sample fluid to the chamber; a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, the sample fluid having a toxin of interest therein; a mechanism for applying a force to the fluids for urging the toxin of interest to pass through the interface into the buffer fluid; a sample fluid outlet coupled to the chamber; and a buffer fluid outlet coupled to the chamber, the buffer fluid being substantially separated from the sample fluid.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

FIG. 1 is a representative system diagram of a separations system according to one embodiment.

FIG. 2 is a representative system diagram of the forces at work in a separations system according to one embodiment.

FIG. 3 is a chart showing the direction of segregation of particles based on their densities and compressibilities relative to the carrier medium.

FIG. 4 is a plot showing the maximum translational velocity of particles of different materials as a function of particle size.

FIG. 5 is a flow diagram of a process according to one embodiment.

FIG. 6 is a flow diagram of a process according to one embodiment.

FIG. 7 is a flow diagram of a process according to one embodiment.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

The following description discloses several preferred embodiments of continuous-flow, fluidic-based separation systems, as well as component parts thereof and/or methods for continuous-flow, fluidic-based separation.

The high-precision, continuous-flow, microfluidic-based techniques described herein address each of the drawbacks encountered by using standard laboratory methods for viral separation by employing physical and chemical mechanisms, such as diffusion mediated, ultrasonic, electrophoretic, dielectrophoretic (DEP), temperature-gradient, and/or isoelectric-focusing techniques to separate and purify biological species from other constituents in the samples. Methods for sample preparation, which may ultimately handle bacteria, viruses, parasites, and toxins, will preferably include combinations of these techniques.

In one general embodiment, a method for separating particles from a sample fluid is comprised of simultaneously passing a sample fluid and a buffer fluid through a chamber such that a fluidic interface is formed between the sample fluid and the buffer fluid as the fluids pass through the chamber, with the sample fluid having particles of interest therein. Also, a force is applied to the fluids for urging the particles of interest to pass through the interface into the buffer fluid, and the buffer fluid is substantially separated from the sample fluid.

In another general embodiment, a method for separating a toxin from a sample fluid is comprised of simultaneously passing a sample fluid and a buffer fluid through a chamber such that a fluidic interface is formed between the sample fluid and the buffer fluid as the fluids pass through the chamber, with the sample fluid having a toxin of interest therein. Also, a force is applied to the fluids for urging the toxin of interest to pass through the interface into the buffer fluid and the buffer fluid is substantially separated from the sample fluid.

In another general embodiment, a system for separating particles from a sample fluid is comprised of a chamber; a sample fluid inlet for introducing a sample fluid to the chamber; a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, with the sample fluid having particles of interest therein; a mechanism for applying a force to the fluids for urging the particles of interest to pass through the interface into the buffer fluid; a sample fluid outlet coupled to the chamber; and a buffer fluid outlet coupled to the chamber, with the buffer fluid being substantially separated from the sample fluid.

In another general embodiment, a system for separating a toxin from a sample fluid is comprised of a chamber; a sample fluid inlet for introducing a sample fluid to the chamber; a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, with the sample fluid having a toxin of interest therein; a mechanism for applying a force to the fluids for urging the toxin of interest to pass through the interface into the buffer fluid; a sample fluid outlet coupled to the chamber; and a buffer fluid outlet coupled to the chamber, with the buffer fluid being substantially separated from the sample fluid.

FIG. 1 shows an embodiment of a system which comprises a chamber 102, sample fluid inlet 104, buffer fluid inlet 106, sample fluid outlet 108, and buffer fluid outlet 110. The sample fluid is supplied to the sample fluid inlet 104, while a pre-selected buffer fluid is supplied to the buffer fluid inlet 106. The sample fluid includes the particles (or a substance, e.g., toxin, chemical, etc.) of interest, while the buffer fluid entering the chamber 102 may not include particles, may include some type of particles, etc. The particles may be added to the sample fluid as part of a medical sample, e.g., from a human; a veterinary sample, e.g., from an animal; and/or a part of an environmental sample, e.g., particles gathered from the environment by any suitable mechanism including filtering air or liquid, swabbing or wiping an object, wash fluid, etc.

The fluids themselves may be any type of fluid, including liquids and gases, and may have any composition. Illustrative fluids or components of the fluids include, but are not limited to water; air; pure liquids (with or without sample mixed therewith); mixtures of liquids; inert gases; reactive gases; medical or veterinary samples such as diluted, modified, or undiluted human or animal bodily fluids (e.g., saliva, urine, blood, etc.); fluids extracted from plants; wash fluid contacted with plants or animals or inanimates (e.g., wash water contacted with spinach or other leafy green vegetables that may be contaminated with *E. coli* O157:H7); etc. The particles of interest may include organic and/or inorganic particles; biological particles, cells, pathogens; etc.

In particularly useful approaches, the systems and methodology described herein may be used to separate pathogens, toxins, cells, and other biological materials from the sample fluid. Illustrative types of toxins include aflatoxin (difurocoumarocyclopentenone and difurocoumarolactone series), saxitoxin, etc. Illustrative types of pathogens include bacteria such as *Bacillus anthracis* (anthrax), *salmonella, streptococcus*; viruses such as hepatitis A and B, influenza, herpes simplex, HIV; protozoa such as *cryptosporidium, plasmodium, giardia lamblia*; fungi such as *candida, histoplasma capsulamtum*; etc.

With continued reference to FIG. 1, in operation, the two fluids are flowed beside each other in a laminar fashion to minimize mixture of the fluids at the interface 112 formed between them. This side-by-side flow permits molecules and particles in the sample liquid to migrate into the buffer liquid at a rate determined in part by the diffusivity of each type of particle, and in part by any additional forces brought to bear on the particles. Since smaller particles tend to migrate faster than larger ones, this results in a rough separation of the particles by size. The smaller particles from the sample liquid migrate into the buffer liquid in the chamber 102 and are carried out through the buffer fluid outlet 110. The sample liquid exits the chamber 102 through the sample fluid outlet 108.

The chamber 102 can also be placed horizontally with the buffer fluid inlet 106 at the upper left so that the flows pass above and below rather than side-by-side. In this configuration, gravity and sedimentation also influence the separation of heavier particles remaining in the lower stream, while smaller particles would migrate more rapidly upwards against the influence of gravity.

To further enhance separation, forces may be applied to one or more of the fluids, in the chamber or away therefrom.

FIG. 2 graphically depicts different forces that may be applied to the fluids in a separation system. To prepare the sample fluid, the sample fluid may first encounter an agitation volume 201, where ultrasonic energy disrupts and/or disassociates particle aggregates that may include virions or other particles adhering to larger particles in the sample fluid. In toxin separations, the agitation volume may be used to dislodge toxins from larger particles. Once leaving the agitation volume 201, the sample fluid will typically include a majority of free particles and is added to the chamber 202, optionally after injection into a sheath flow to minimize sample-wall interactions.

As shown, in one approach, an acoustic reflector 204 is positioned on one side of the chamber 202 while a wave emitter 206 such as a piezoelectric actuator, ultrasonic wave emitter, etc. is positioned on the opposite side of the chamber 202. In one preferred approach, the wave emitter 206 is used to generate a lowest-order, transverse ultrasonic standing wave in the chamber 202. The acoustic radiation forces 214 on the particles act to confine them at the acoustic pressure node 220 on one side of the chamber 202 cross section. Since these forces are typically proportional to the third power of the particle radius, they are felt much more by the larger particles than by the smaller particles, thus enhancing size-based separation. The influence of this standing wave is combined with that of the diffusive separation. Also, the standing wave acts preferentially on particles that are more dense or incompressible, so it can serve to retard the diffusion of the larger and denser particles in the sample fluid while letting the smaller, less dense particles migrate into the buffer fluid, thereby enhancing the performance of the overall separation process. This one-dimensional force is based on the compressidensity factor of the fluid, as calculated by Equation 1:

$$\phi=G_\rho-G_\beta \qquad \text{Equation 1}$$

where $\phi$ is the compressidensity factor and is derived from differences in the compressibility and density, and $G_\rho$ (density difference) and $G_\beta$ (compressibility difference) are as defined in the following equations:

$$G_\rho = 3\left(\frac{\rho_c - \rho_f}{\rho_c + 2\rho_f}\right) \qquad \text{Equation 2}$$

$$G_\beta = \left(1 - \frac{\beta_C}{\beta_f}\right) \qquad \text{Equation 3}$$

where $\rho_c$ is the density of the solute, $\rho_f$ is the density of the fluid, $\beta_c$ is the compressibility of the solute, and $\beta_f$ is the compressibility of the fluid.

In another approach, electrodes 210 may be placed on each side of the chamber 202 to generate an electric field across the chamber 202. The electric field may be either Direct Current (DC) or Alternating Current (AC), and may have many different characteristics. As described in more detail below, the electric field generates electrophoretic and/or dielectrophoretic forces 212 that urge certain particles to cross (or not cross) the interface between the fluids. In other words, the particles will be attracted or repelled based on the phenomena of electrophoresis and/or dielectrophoresis. Because the effects will be different for different particle types, the particles can be manipulated in the fluidic flow.

These effects will also differ depending on additional parameters such as dielectric polarizability, pH, conductivity, fluid and ambient temperature, and/or zeta potential. Each of these parameters may be adjusted to produce a desired effect. Therefore, prior to attempting the separations, the physical properties that distinguish and enable separation of one species from another are preferably determined for each of the target species (such as viral compressidensity factors, surface charge, zeta potential, dielectric polarizability as a function of the electromagnetic frequency, etc.).

In the case of separation of biological samples in non-acidic solutions (e.g. solution pH of 7 or snore), the electrophoretic force 212 on the (typically negatively charged) biological (viral and bacterial) particles causes them to migrate toward the buffer flow region. Since the electrophoretic mobility tends not to be a function of the particle size but only the net charge (zeta potential), the biological particles are drawn into the buffer, further enriching the concentration of such particles in the buffer solution. At the lower end of the chamber 202, the flow is divided, with the biological-particle-enriched buffer flowing down to the right through the buffer fluid outlet 218, while the non-biological particle contaminants flow down to the left out the sample fluid outlet 216.

In a particularly preferred approach, as alluded to in FIG. 2, a combination of diffusive, sonic (e.g., ultrasonic), and electrophoretic forces may be used to enhance the selective separation of particles or substances of interest from the sample fluid into the buffer fluid.

When multiple fields and functionalities are combined in this way, the action of the diffusive separator can be greatly modified and enhanced in terms of purification and concentration. Enhanced purification or concentration improves the performance of subsequent uses of the particle of interest. Subsequent uses can include more than just detection and characterization, such as growth, propagation, etc. This enables the multi-field separator to process large samples of liquid in a flow-through manner with high efficiency and speed. It can also perform challenging separation tasks, such as the separation of very small particles (such as viruses) from a complex mixture of other particles in an efficient manner.

The separation techniques described herein are preferable to mechanical separations for several reasons. For example, damage to the particles of interest is minimized because a filter or surface is not used to collect the particles of interest. Typically, removal of particles of interest from a filter or surface can damage the particles, whereas in this approach, there is no removal necessary as the particles are present in the buffer fluid, not on a surface.

Figure 5:
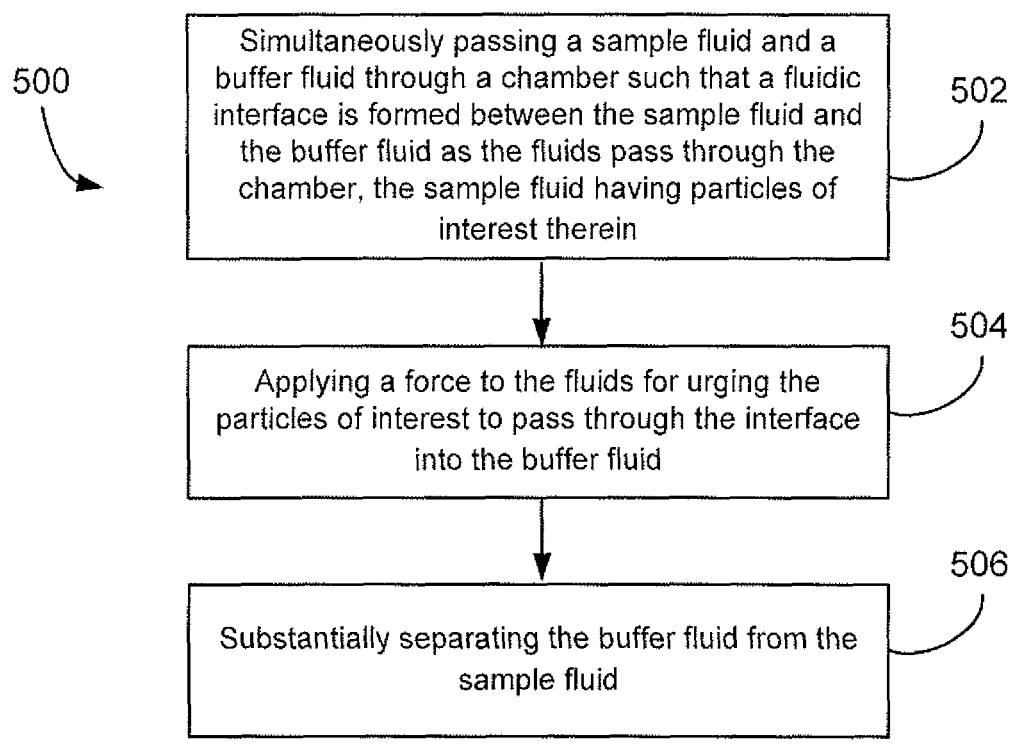

FIG. 5 illustrates a method 500 according to one embodiment. As an option, the present method 500 may be implemented in the context of the functionality and architecture of FIGS. 1-2. The present method 500 may also be carried out in any desired environment, and any of the aforementioned definitions may apply during the present description.

Still referring to FIG. 5, in operation 502, two fluids are passed through a chamber such that an interface between the two fluids is formed. In a preferred embodiment, this interface minimizes mixing of the two fluids, and the flow is maintained as laminar to minimize mixing of the two fluids. Also, a sample fluid includes a particle or particles of interest. One or more types of particles can be targeted for separation from the sample fluid. The greater the distance traveled in the chamber with the two fluids passing side-by-side, the greater the diffusion of the particle or particles of interest into the buffer fluid.

In operation 504, a force is applied to the fluids to urge the particles of interest to pass through the interface and into the buffer fluid. In one embodiment, a force can be based on electrophoresis, which tends to cause charged particles to move in a desired direction by applying a constant or quasi-constant uniform magnetic field across a chamber. An electric field applied to particles will tend to attract particles with a net negative charge toward the positive electrode and will tend to attract particles with a net positive charge toward the negative electrode.

In another embodiment of operation 504, a force can be based on dielectrophoresis, where the frequency can be tuned. In dielectrophoresis, an alternating current (AC) field can be applied to the fluids with a gradient in the field that may be tuned to attract particles to a high field region, or to repel particles from a high field region, depending on the desired effect on the particles in the fluids.

In another embodiment of operation 504, a force can be sonic in nature (e.g., ultrasonic) and can be used to focus larger particles toward a cross section of the sample fluid stream traveling through a chamber, thus reducing the amount of larger particles which will migrate into the buffer fluid.

In another embodiment of operation 504, a force can be gravitational in nature, where the fluids are passed above and below each other, with the buffer fluid flowing above the sample fluid. This tends to cause the heavier particles to sink in the sample fluid, which tends to reduce the amount of heavier particles which migrate into the buffer fluid.

In operation 506, the buffer fluid is substantially separated from the sample fluid. In practice, some mixing will occur between the buffer fluid and the sample fluid, and an exact separation probably will not be possible because of this mixing. Therefore, in the context of operation 506, substantially separating means separating the fluids to as great of a degree as is possible taking into account natural tendencies toward mixing of the fluids as they pass through a chamber side-by-side or one above the other. In one embodiment, the separation is accomplished by splitting the flow at the interface so that each fluid passes into a separate flow path.

As mentioned above, the systems and methods are not limited to the separation of particles. Rather, molecules, compounds, and complexes of interest may be separated using similar techniques. For instance, a toxin of interest may be separated from a sample fluid using the systems of FIGS. 1 and 2 using the techniques described above, with or without modification. In addition, the buffer fluid may be any receiving fluid that is appropriate for the separation procedure, and is not limited in any way to only "buffers." Likewise, the sample fluid may be any fluid that contains particles of interest, or particles that are not of interest.

Figure 6:
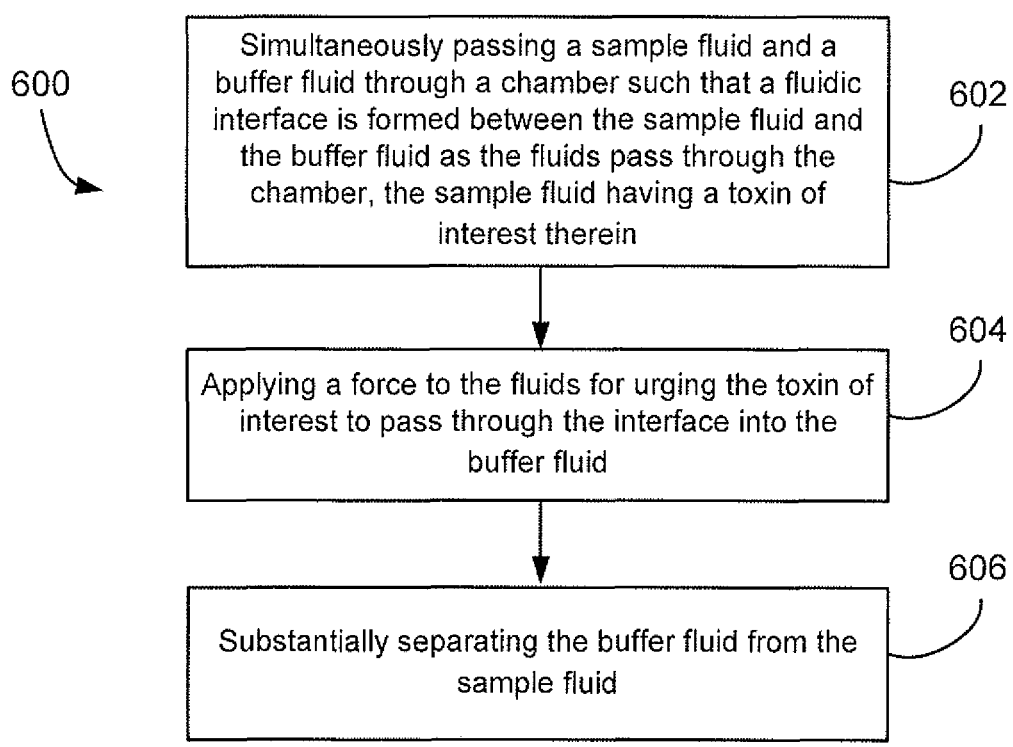

FIG. 6 illustrates a method 600 according to another embodiment. As an option, the present method 600 may be implemented in the context of the functionality and architecture of FIGS. 1-2 and 5. The present method 600 may also be carried out in any desired environment, and any of the aforementioned definitions may apply during the present description.

With continued reference to FIG. 6, in operation 602, a sample fluid and a buffer fluid are simultaneously passed through a chamber such that a fluidic interface is formed between the fluids. In this embodiment, the sample fluid includes one or more toxin(s) of interest.

In operation 604, a force is applied to the fluids to urge the toxin or toxins of interest to pass from the sample fluid through the interface and into the buffer fluid. A force includes any of the previously described forces used in operation 504. In a particularly preferred embodiment, the force is ultrasonic or acoustic in the nonlinear or "streaming" regime of the acoustic forces is applied to the fluids to urge particles of interest in a desired direction.

In operation 606, the buffer fluid is substantially separated from the sample fluid. In practice, some mixing will occur between the buffer fluid and the sample fluid, and an exact separation probably will not be possible because of this mixing. Therefore, in the context of operation 606, substantially separating means separating the fluids to as great of a degree as is possible taking into account natural tendencies toward mixing of the fluids as they pass through a chamber side-by-side or one above the other. In one embodiment, the separation is accomplished by splitting the flow at the interface so that each fluid passes into a separate flow path to exit a chamber.

Figure 7:
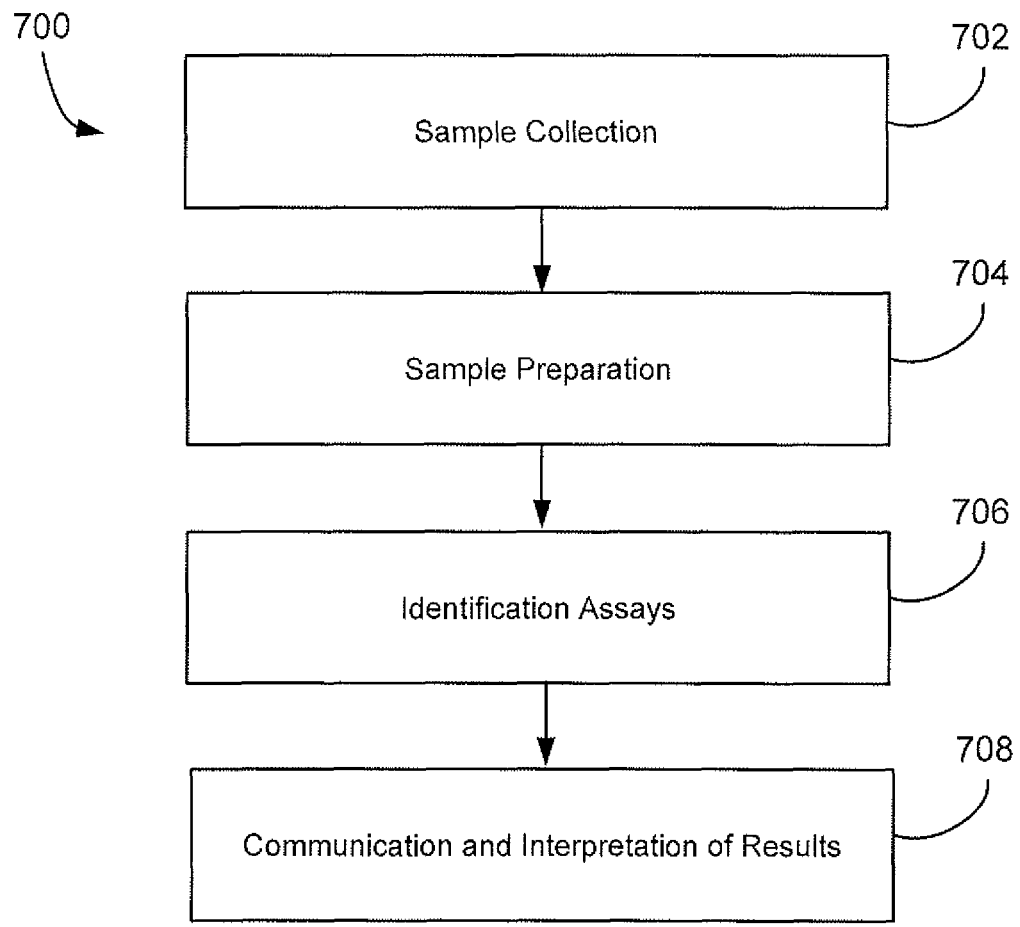

FIG. 7 illustrates a general method 700 for collection, handling, and manipulation of samples for determining physical and/or chemical characteristics of a sample. As an option, the present method 700 may be implemented in the context of the functionality and architecture of FIGS. 1-2, 4 and 5. The present method 700 may also be carried out in any desired environment, and any of the aforementioned definitions may apply during the present description.

With continued reference to FIG. 7, in operation 702, a sample is collected from a source or multiple sources such as air, food, water, skin, clothing, surfaces, blood, oral cavities, etc. A sample can be collected from any physical state including solid, gaseous, liquid, vapor, etc.

In operation 704, a sample is prepared according to criteria which will determine what is to be discovered about the sample. For example, the sample can be prepared by purifying or separating a desired portion of the sample from the rest, or concentrating the sample to enhance the presence of a desired portion. Other optional preparation techniques include mixing it with another material, incubating it to promote growth, heating it to cause faster reactions, growth, or state changes, cleaning it to remove debris or unwanted particulates, etc.

In operation 706, identification assays are developed for detecting the desired portion of the sample. In one embodiment, the identification assays include immuno assays, nucleic-acid assays, mass-spectrometer assays, etc.

In operation 708, the results of operations 702, 704, and 706 are interpreted according to known physical and chemical characteristics of elements, compounds, and mixtures, etc. Results are also communicated through proper channels so that action can be taken to correct the problem discovered through method 700. For example, if a highly contagious and dangerous pathogen is isolated and classified as a result of method 700 then the Center for Disease Control and/or other health authorities may be contacted so that the release might be contained and harm to life reduced. In another embodiment, an alert or alarm may be sounded automatically inside a building or room once a particular particle is detected from using; method 700. Further, the alert or alarm may automatically notify authorities of the detection of the pathogen, toxin, or other particle of interest.

The illustrative systems and methods described herein have broad application to a plethora of uses. For example, a device based on the teachings herein may be used for the automated extraction and concentration of pathogens (infectious particles) from medical, veterinary, or environmental samples for purposes of detection. This use is important for the detection and identification of biological warfare agents or agents causing widespread disease. It may be used as a stand alone technology to aid in sample preparation, or it may be included as part of a larger system for automated detection for homeland security, national defense, quality control of food products or water supply, etc.

An illustrative example of how these techniques may be used in testing equipment would be as autonomous systems that could monitor air filters from international-flight airplanes or as handrails at international airports, serving as sentinel systems that monitor the appearance and transmission of aerosol-transmitted pathogens (such as influenza, H5N1, SARS, etc.). Another example of an embodiment is a handheld or portable system capable of being used by first responders in an emergency situation to detect airborne pathogens and biothreats.

In other approaches, a device may be used for the extraction and concentration of pathogens, cells, or other particles of interest from clinical samples for purposes of medical diagnosis or evaluation. The same technology can be applied to the separation of particles in many other fields of use.

In one illustrative embodiment, a biothreat detection system and method according to one embodiment continuously samples the surrounding air by drawing the air in at some predetermined rate, e.g., 1000 liter/min, and impinging a selected portion of the air into a liquid sample fluid. The sizes of particles within the solution are then measured using any suitable technique or device. One such device is the Aerodynamic Particle Sizer manufactured by TSI, Inc. If the instrument detects particles in a particular size range an alarm is triggered and the operator determines if additional testing is required. Additional testing begins with the determination of the presence of adenosine triphosphate (ATP) using a bioluminometer, indicating the presence of certain biological materials. Additional technologies known in the art may be used to determine if components within a cloud are biological in nature by measuring the elastic scattering and fluorescence signals from particles passing through the detector. In one approach, before a sample is run through a detection/identification system, a determination is made that the cloud does indeed contain biological material. In another approach, the sample is run through the system without such a determination.

Figure 2:
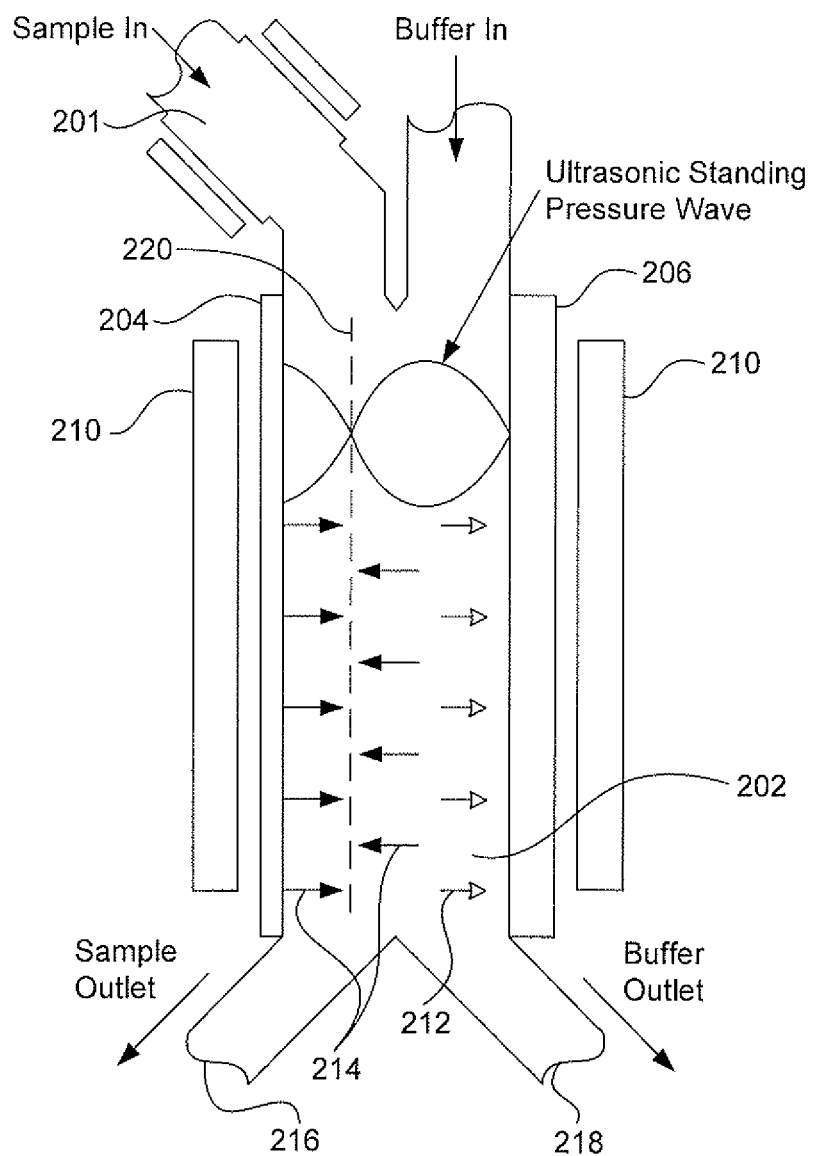

The biothreat detection system and method collects a sample from a cloud, optionally after it has been determined to contain biological material; concentrates the sample using existing air sampling technology; incubates the collected particles to antibodies attached to magnetic beads and/or fluorescent dyes; sorts particles attached to magnetic beads from other particles using MACS (magnetic cell separation systems) and/or runs the sample through a flow cytometer (FCM) system which may include the separation system as described herein, e.g., with reference to FIGS. 1 and 2, to obtain an identification based on particle size (organism+ magnetic bead) or attached fluorochrome, and to sort the particles for characterization (which can be through a process such as a Polymerase Chain Reaction); processes the sample for Polymerase Chain Reaction (PCR) and performs a PCR assay to confirm the initial identification obtained using a flow cytometer (FCM) system to protect against false positives.

PCR products may be analyzed electrophoretically, but automated methods based on DNA hybridization may be used to analyze products, and may be incorporated into an instrument containing some or all of the above-mentioned components.

In one approach, air-collected samples may be manually introduced into the FMC and then the buffer fluid manually transferred to further sample preparation and PCR. In another approach, the process is primarily or fully automated. In one embodiment, samples collected for this type of system may be from the air and are concentrated and sorted by using magnetic antibodies, so therefore will probably not contain much dirt or other contaminating material except for aggregates that will be disrupted by exposure to an acoustic energy wave.

Accordingly, the systems described herein may form part of a robust, miniaturized method for virus extraction, concentration, and detection of both known and unknown viruses from clinical and laboratory samples that can replace low-throughput, traditional methods. Further, multi-field separation devices may be created, in order to achieve high efficiencies in a single platform, capable of very high throughput.

In one approach, the physical and biochemical properties of pathogenic viruses are analyzed using simulations coupled to and validated by experimental data. Once the unique properties are identified, a microfluidic separator and assay system may be created using the teachings herein.

In another approach, a system analyzes a clinical sample for viruses, and may be designed to mate with an emerging multiplex assay. Further, such a system may allow detection of any novel viruses as well. Additionally, genetic characterization of viral families normally present in clinical or environmental samples may yield valuable information about the viral flora that is present in a given sample. This information expedites the detection of abnormal specimens and genetic "turnover" in complex microbial communities.

Such a technique may also eliminate the need for the bioinformatics group to identify three regions per pathogen signature (two TaqMan primers and one probe, as is used, today, in Lawrence Livermore National Laboratory's CBNP MUX group and others) per assay. Instead, signature requirements may be limited to identification of a single 38-50 nucleotide region with approximately 10% degeneracy. Accordingly, one embodiment tests a Multiplex Ligation-Dependent Probe Amplification (MLPA) sample for the identification of conserved viral sequences characteristic of viral families. RNA viruses have an extremely high mutation rate in their RNA sequences and this can make identification of partial or 100%-conserved region characteristic of viral subgroups (i.e. genera) very difficult. Even members of a single species may contain no 100%-conserved regions longer than 20 RNA bases. MLPA reduces the number of bases required for signature development and allows a small percentage of mismatches to be present within that region without affecting detection capabilities.

The following sections describe the science behind some of the technology useable in conjunction with various embodiments of the present invention.

Ultrasonics

The availability of high-frequency ultrasonic sources such as piezoelectric ceramic elements has allowed very large acoustic energy densities to be generated with very precise control. The force on a particle within a one-dimensional (1-D) acoustic standing wave field is called the acoustic radiation force, given by Equation 4:

$$F_o = -\frac{1}{4}V_0 \cdot \frac{P_A^2}{\rho_m c_m^2} \cdot k\sin(2kx) \cdot (G_\rho - G_\beta) \quad \text{Equation 4}$$

Note that the magnitude of the force is proportional to $V_0$, the volume of the particle (assumed spherical). The second term is the time averaged acoustic energy density at the location of the particle, where $P_A$ is the pressure amplitude of the oscillating sound field, and $\rho_m$ and $c_m$ are the density and sound speed of the suspending medium, respectively. The sound wave is taken to be aligned along the x-axis, so the third term describes the sinusoidal nature of the standing wave, where the wavenumber k is defined by Equation 5:

$$k = 2\pi/\lambda \quad \text{Equation 5}$$

Where k is the wavenumber and $\lambda$ is the wavelength.

The final term in Equation 4, in parenthesis, concerns the relative densities and compressibilities of the particle and the medium. It is this term that describes how the magnitude and direction of the force varies depending on these physical properties of a particular particle. The term is sometimes referred to as the "compressidensity factor," and is defined in Equations 1-3 above.

For most solid particles suspended in gaseous or liquid media, the sign of the compressidensity factor is such that the force acts to push the particles toward minima of pressure amplitude; that is, toward the pressure nodes of the standing wave. The situation for air bubbles, lipids (fats, oils, etc.), or other highly compressible fluids in a liquid medium is reversed, and these tend to migrate toward pressure antinodes. Most biological particles in the solutions that they are normally analyzed in, such as cells and viruses, are somewhat denser than the aqueous medium that suspends them, and less compressible. Therefore, they tend to segregate to pressure nodes, as illustrated in FIG. 3.

Figure 3:
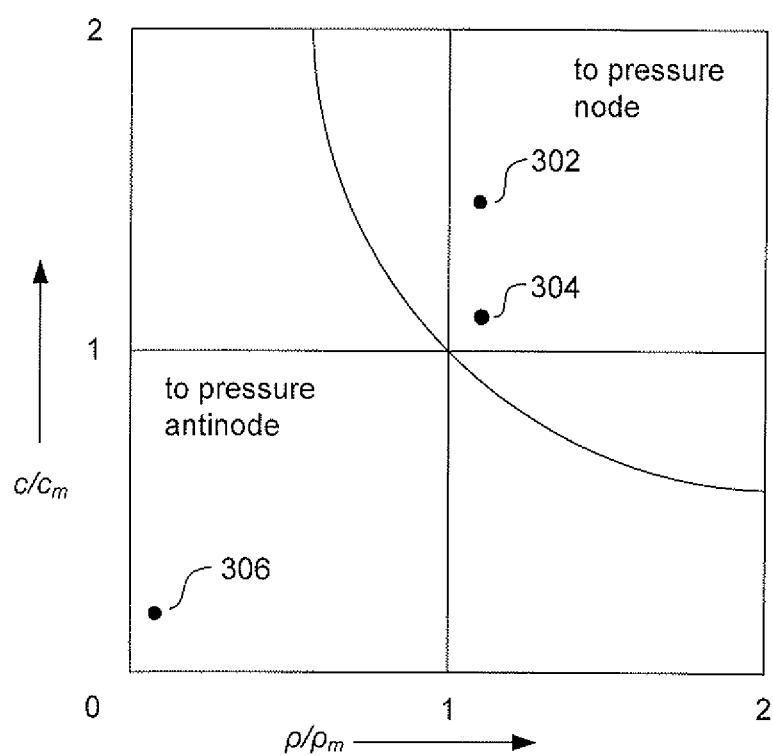

FIG. 3 is a chart showing the direction of segregation of particles based on their densities and compressibilities relative to the medium, assumed to be water. Point 302 corresponds to polystyrene microspheres, point 304 to erythrocytes, and point 306 to air bubbles. Viruses having small volumes and specific gravities between about 1.1 to 1.3, are likely to occupy the region somewhat to the right of points 302 and 304.

When employed for purposes of particle separation, ultrasonic forces have generally been used to segregate particles to one or more pressure nodes across the width of a fluid channel. This creates a "stripe" or streamline of concentrated particles. A downstream flow divider is then used to separate the segregated particles from the clarified liquid. The maximum forces generated with a 3 MHz standing wave with pressure amplitude of 1.0 Mpa are equivalent to those provided by a 160-g acceleration. While this is considerably lower than the accelerations possible in an ultracentrifuge, the required travel distances are typically only about a few hundred μm, therefore allowing very rapid separation for longer particles.

The challenge with this approach is often one of fabrication. In order for the separation to occur in the same plane as the flow division, it is necessary to set up a standing wave that runs transversely across the channel. In a planar microfabricated device, this can be difficult to achieve, as it requires integrating piezoelectric transducers to the chamber sidewalls. One way to overcome this problem is by the use of phased co-planar transducers. Multiple transducers located on one side of the chamber can be driven with out-of-phase electrical signals, thus setting up a transverse oscillation equivalent to a typical standing wave. This approach also allows the creation of standing wave fields tailored to a particular application. Fractionation of a mixture of different particles is achievable because the relative strengths of the acoustic radiation force will be different for different particles. Assuming that the particles are not so different that they segregate in opposite directions (such as with, for instance, blood cells and air bubbles) they can still be separated based on the speed of their movement. The "mobility" of a particle within a standing wave is determined by the balance between the acoustic radiation force and the opposing fluidic (i.e. Stokes) drag, given by Equation 6.

$$F_d = 6\pi\mu r v \quad \text{Equation 6}$$

where $F_d$ is fluidic drag, $\mu$ is the viscosity coefficient, r is the radius of the particle, and v is the translational velocity of the particle toward a pressure node. As the acoustic radiation force is a strong function of particle radius, the translational velocity of a particle toward a pressure node will be a strong function of the particle size (as well as its properties).

Figure 4:
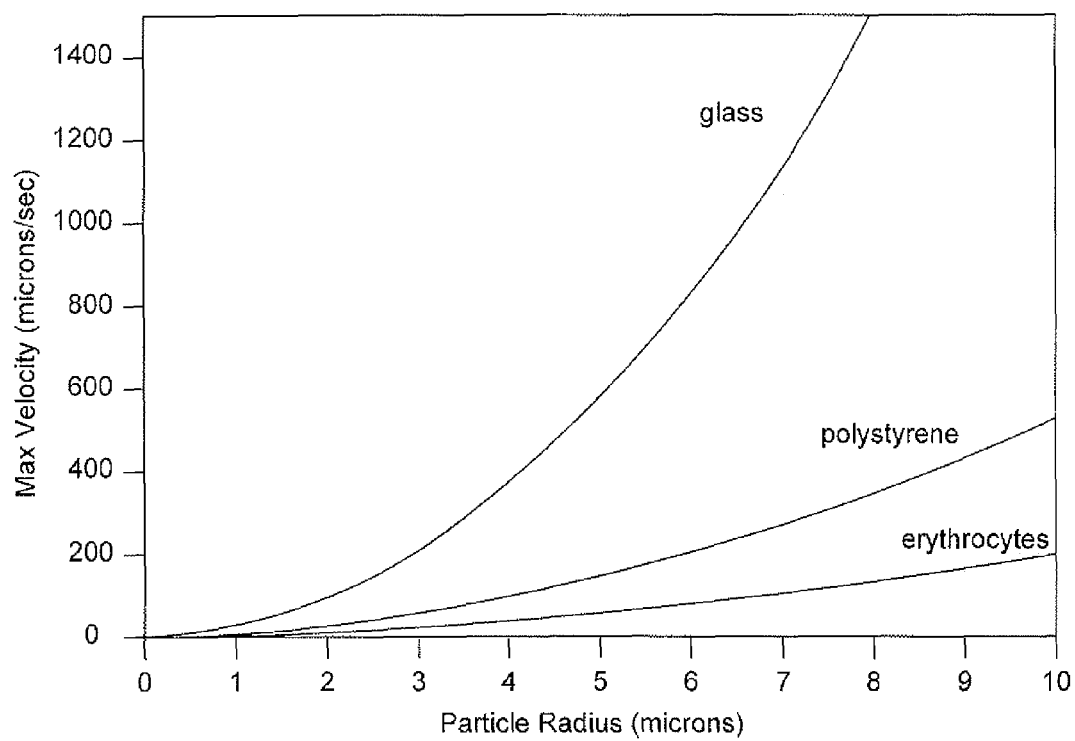

FIG. 4 is a plot showing the maximum translational velocity of particles of different materials within a 1 MHz, 300 KPa ultrasonic standing wave, as a function of particle size. As shown in FIG. 4, inorganic and even "soft" biological particles such as erythrocytes (approximately 6 μm in diameter) move fairly quickly in a typical 1 MHz standing wave in water, while particles the size of viruses (less than approximately 0.1 μm) move relatively little. For this reason, it is much easier to manipulate cells and other μm-scale objects than viruses; an ultrasonic separator can therefore be used to selectively concentrate and remove larger particles while allowing viruses to pass.

Dielectrophoresis

Dielectrophoretic (DEP) forces can be used to extract particles from a flowing stream. The dielectrophoretic force is generated when an electric dipole is established in a particle. When placed in a non-uniform electric field, the particle will move to areas of high or low field strength depending on the relative complex permittivities of the particle and the suspending fluid. The dielectrophoretic force on a spherical particle can be expressed as:

$$F_{DEP} = 2\pi \in_m r^3 Re\{f_m\} \nabla(\underline{E}_{rms}^2) \quad \text{Equation 7}$$

where $\in_m$ is the permittivity of the medium in which the particle is suspended, $f_m$ is the Clausius-Mossoti factor, a is the particle radius and $\underline{E}$ is the rms electric field vector. For the dipolar contribution, the Clausius-Mossoti factor is expressed as:

$$f_m = \frac{(e_p^* - e_m^*)}{(e_p^* + 2e_m^*)} \quad \text{Equation 8}$$

where $e_p^*$ is the complex permittivity of the particle given by $e_p^* = e - js/w$, where e is as before, s is the conductivity, and w is the frequency of the applied field. Likewise, $e_m^*$ is the complex permittivity of the suspending medium. The Clausius-Mossoti factor determines the sign of the DEP force, i.e., positive (trapping) or negative (levitation) DEP forces. For any polarizable species, such as, biological species, the frequency can be manipulated to effect positive or negative DEP, which enables preferential manipulation of target species via the applied field frequency.

The use of DEP forces becomes practical in microfluidic devices with aqueous media because field strengths at sufficient intensities are achievable at sub-millimeter dimensions with only a few volts applied to the electrodes, thus avoiding electrolysis of water (which could disrupt processing because of the gas bubbles that are formed). A chief advantage to using dielectrophoresis is that it is a simpler, reagentless technique for particle extraction for a fluid.

Positive dielectrophoretic forces have been demonstrated for collecting 1-μm-diameter *Bacillus globigii* and *Erwinia herbicola* on interdigitated electrodes spacing operating at about 5 VAC. This work can be extended to capture viruses. Viruses such as smallpox viruses have lengths on the order of 50-200 nm. Since DEP forces are proportional to the cubic of the characteristic length of the particle, capturing small viruses using DEP is a challenge. Recent electrodes have been demonstrated to operate at 50 VAC at about 1 MHz, a factor of 10 over former electrodes. AC DEP forces can be used in the chamber to trap viruses. If the viruses exhibit positive DEP forces at high frequencies and if the operating voltages are pushed higher and the electrodes spacing is reduced then viruses may be trapped using Alternating Current (AC) DEP. In a preferred embodiment, Alternating Current (AC) DEP comprising generating a non-linear electric field by patterning pillars in an electrophoretic separation channel inside the chamber can be used to trap viruses.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for separating particles from a sample fluid, comprising:

simultaneously passing a sample fluid and a buffer fluid through a chamber such that a fluidic interface is formed between the sample fluid and the buffer fluid as the fluids pass through the chamber, the sample fluid having particles of a first characteristic and particles of a second characteristic therein;

applying at least one of an electrophoretic and a dielectrophoretic force to the fluids for urging the particles of the first characteristic to pass through the interface into the buffer fluid;

applying an acoustic force to the fluids for urging the particles of the second characteristic to remain in the sample fluid; and substantially separating the buffer fluid from the sample fluid;

wherein the particles of the second characteristic substantially remain in the sample fluid during the separation.

2. A method as recited in claim 1, orienting the chamber so that a gravitational force is applied to the fluids for urging particles of a third characteristic and/or the particles of the second characteristic also having the third characteristic to remain in the sample fluid.

3. A method as recited in claim 1, wherein the particles of the first characteristic and/or the particles of the second characteristic are pathogens.

4. A method as recited in claim 1, wherein the fluids pass through the chamber at about a same velocity as measured at the interface.

5. A method as recited in claim 1, wherein the sample fluid also includes other particles, wherein the particles of the first characteristic are associated with the other particles, wherein applying the acoustic force to the fluids substantially causes the particles of the first characteristic to dissociate from the other particles, and wherein the other particles substantially remain in the sample fluid after applying the force to the fluids.

6. A system for separating particles from a sample fluid, comprising:

a chamber;

a sample fluid inlet for introducing a sample fluid to the chamber;

a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, the sample fluid having particles of a first characteristic and particles of a second characteristic therein;

a mechanism for applying at least one of an electrophoretic and a dielectrophoretic force to the fluids for urging the particles of the first characteristic to pass through the interface into the buffer fluid;

a mechanism for applying an acoustic force to the fluids for urging the particles of the second characteristic to remain in the sample fluid;

a sample fluid outlet coupled to the chamber; and a buffer fluid outlet coupled to the chamber, the buffer fluid being substantially separated from the sample fluid;

wherein the particles of the second characteristic substantially remain in the sample fluid during the separation.

7. A system as recited in claim 6, wherein the mechanism for applying the acoustic force to the fluids comprises:
two or more phased co-planar transducers positioned on one side of the chamber; and
an acoustic reflector positioned on a side of the chamber opposite the two or more phased co-planar transducers; and
wherein the mechanism for applying at least one of the electrophoretic force and the dielectrophoretic force comprises:
a first electrode positioned on a same side of the chamber as the two or more phased co-planar transducers; and
a second electrode positioned on the side of the chamber opposite the two or more phased co-planar transducers.

8. A system as recited in claim 6, wherein the fluids pass through the chamber at about a same velocity as measured at the interface.

9. A system as recited in claim 6, wherein the sample fluid also includes other particles,
wherein the particles of the first characteristic are associated with the other particles,
wherein applying the acoustic force to the fluids substantially causes the particles of the first characteristic to dissociate from the other particles, and
wherein the other particles substantially remain in the sample fluid after applying the force to the fluids.

10. A system as recited in claim 6, further comprising a mechanism for selectively applying a gravitational force to the fluids, wherein applying the gravitational force to the fluids urges particles of a third characteristic and/or the particles of the second characteristic also having the third characteristic to remain in the sample fluid.

11. A system for separating particles from a sample fluid, comprising:
a chamber;
a sample fluid inlet for introducing a sample fluid to the chamber;
a buffer fluid inlet for introducing a buffer fluid to the chamber, wherein a simultaneously-introduced sample fluid and buffer fluid pass through the chamber such that a fluidic interface is formed between the sample fluid and the buffer fluid as the fluids pass through the chamber, the sample fluid having particles of a first characteristic and particles of a second characteristic therein;
a mechanism for applying at least one of an electrophoretic and a dielectrophoretic force to the fluids for urging the particles of the first characteristic to pass through the interface into the buffer fluid;
a mechanism for applying an acoustic force to the fluids for urging the particles of the second characteristic to remain in the sample fluid;
a sample fluid outlet coupled to the chamber;
a buffer fluid outlet coupled to the chamber, the buffer fluid being substantially separated from the sample fluid; and
wherein the mechanism for applying the acoustic force to the fluids comprises:
a wave emitter positioned on one side of the chamber for creating a standing wave that runs transversely across the chamber;
an acoustic reflector positioned on a side of the chamber opposite the wave emitter; and
wherein the mechanism for applying at least one of the electrophoretic force and the dielectrophoretic force comprises:
a first electrode positioned a same side of the chamber as the wave emitter; and
a second electrode positioned on the side of the chamber opposite wave emitter.

12. A method as recited in claim 2, wherein the second characteristic is selected from the group consisting of: a particle volume greater than the particle volume of the particles of the first characteristic, a particle surface area greater than the particle surface area of the particles of the first characteristic, and
wherein the third characteristic is selected from the group consisting of: a particle mass greater than the particle mass of the particles of the first characteristic, and a capacity for sedimentation greater than the capacity for sedimentation of the particles of the first characteristic.

13. A system as recited in claim 10, wherein the second characteristic is selected from the group consisting of: a particle volume greater than the particle volume of the particles of the first characteristic, a particle surface area greater than the particle surface area of the particles of the first characteristic, and
wherein the third characteristic is selected from the group consisting of: a particle mass greater than the particle mass of the particles of the first characteristic, and a capacity for sedimentation greater than the capacity for sedimentation of the particles of the first characteristic.

14. A method as recited in claim 1, wherein applying the acoustic force urges the particles of the second characteristic toward an acoustic pressure node in the sample fluid.

15. A method as recited in claim 14, wherein the acoustic force is an ultrasonic force.

16. A method as recited in claim 1, wherein the acoustic force creates a transverse standing wave in the fluids.

17. A system as recited in claim 6, wherein the acoustic force is for urging particles of the second characteristic toward an acoustic pressure node in the sample fluid.

18. A system as recited in claim 17, wherein the acoustic force is an ultrasonic force.

19. A system as recited in claim 6, wherein the ultrasonic force creates a transverse standing wave in the fluids.

20. A system as recited in claim 11, wherein the acoustic force urges the particles of the second characteristic toward an acoustic pressure node in the sample fluid.

21. A system as recited in claim 20, wherein the acoustic force is an ultrasonic force.

22. A system as recited in claim 21, wherein the ultrasonic force creates a lowest order, ultrasonic transverse standing wave in the fluids.

23. A method as recited in claim 1, further comprising:
separating particles of interest from the buffer fluid;
identifying the particles of interest; and
alerting a relevant authority upon determining that the particles of interest are dangerous particles.

24. A system as recited in claim 11, further comprising:
a mechanism for separating particles of interest from the buffer fluid;
a mechanism for identifying the particles of interest; and
a mechanism for alerting a relevant authority upon determining that the particles of interest are dangerous particles.

25. A method for separating particles from a sample fluid, comprising:
simultaneously passing a sample fluid and a buffer fluid through a chamber such that a fluidic interface is formed between the sample fluid and the buffer fluid as the fluids pass through the chamber, the sample fluid having panicles of a first characteristic and particles of a second characteristic therein;

applying at least one of an electrophoretic and a dielectrophoretic force to the fluids for urging the particles of the first characteristic to pass through the interface into the buffer fluid;

applying an acoustic force to the fluids for urging the particles of the second characteristic to remain in the sample fluid;

allowing a gravitational force to the fluids to urge the particles of the second characteristic to remain in the sample fluid;

substantially separating the buffer fluid from the sample fluid;

wherein the fluids pass through the chamber at about a same velocity as measured at the interface, wherein at least one of the particles of the first characteristic and the particles of the second characteristic are pathogens, wherein the particles of the second characteristic substantially remain in the sample fluid during the separation, wherein the sample fluid also includes other particles, wherein the particles of the first characteristic are associated with the other particles, wherein applying the acoustic force to the fluids substantially causes the particles of the first characteristic to dissociate from the other particles, wherein the other particles substantially remain in the sample fluid after applying the force to the fluids, wherein the second characteristic is selected from the group consisting of: a particle volume greater than the particle volume of the particles of the first characteristic, and a particle surface area greater than the particle surface area of the particles of the first characteristic, wherein the acoustic force is an ultrasonic force, wherein the ultrasonic force creates a transverse standing wave in the fluids, and wherein the transverse standing wave urges the particles of the second characteristic toward an acoustic pressure node in the sample fluid.

* * * * *